(12) United States Patent
Chinnock

(10) Patent No.: US 7,448,753 B1
(45) Date of Patent: Nov. 11, 2008

(54) PORTABLE DIGITAL MEDICAL CAMERA FOR CAPTURING IMAGES OF THE RETINA OR THE EXTERNAL AUDITORY CANAL, AND METHODS OF USE

(76) Inventor: Randal B. Chinnock, 243 S. St., Southbridge, MA (US) 01550

( * ) Notice: Subject to any disclaimer, the term of this patent is extended or adjusted under 35 U.S.C. 154(b) by 301 days.

(21) Appl. No.: 11/458,610

(22) Filed: Jul. 19, 2006

Related U.S. Application Data

(60) Provisional application No. 60/700,513, filed on Jul. 19, 2005.

(51) Int. Cl.
A61B 3/14 (2006.01)
(52) U.S. Cl. .................. 351/206; 351/214; 396/18
(58) Field of Classification Search ............ 351/206, 351/214; 396/18
See application file for complete search history.

(56) References Cited

U.S. PATENT DOCUMENTS 4,834,526 A * 5/1989 Nunokawa .................. 351/206

2004/0174498 A1 * 9/2004 Zorn et al. .................. 351/214
2006/0256286 A1 * 11/2006 Nishio et al. ................ 351/211

* cited by examiner

*Primary Examiner*—Jordan M Schwartz
(74) *Attorney, Agent, or Firm*—Brian M. Dingman; Mirick, O'Connell, DeMallie & Lougee

(57) ABSTRACT

A hand-held digital camera for obtaining images of a portion of a patient's body and having a hand-held housing, a visible light source located within the housing for providing light along an illumination path from the housing aperture to the patient's body, an image sensor located within the housing that detects light returning from the patient's body along an imaging path that passes into the housing aperture, an optical system located within the housing with separate illumination and imaging paths, an external optical aperture common to the illumination and imaging systems, wherein the illumination and imaging sub-apertures are wholly contained within the common external aperture, are longitudinally coincident, and are laterally separated and non-overlapping, a digital memory device for storing captured images, an output display carried by the housing, and the ability to electronically transmit stored images. The camera can be used for retinal imaging and for otoscopy.

47 Claims, 14 Drawing Sheets

PORTABLE DIGITAL MEDICAL CAMERA FOR CAPTURING IMAGES OF THE RETINA OR THE EXTERNAL AUDITORY CANAL, AND METHODS OF USE

CROSS-REFERENCE TO RELATED APPLICATION

This application claims priority of Provisional application Ser. No. 60/700,513 filed on Jul. 19, 2005, the disclosure of which is incorporated herein by reference.

GOVERNMENT RIGHTS

This invention was made with Government support under (Grant Number 2 R44 EY 13492-02) awarded by the National Bye Institute. The Government has certain rights in the invention. The inventor is an employee of the assignee, Optimum Technologies, Inc. of Southbridge, Mass.

FIELD OF THE INVENTION

This invention relates to a digital camera that is adapted to capture high-quality images of the retina and/or the external auditory canal of the ear, and transmit the images to an expert at a remote location, and to methods by which such a camera is used.

BACKGROUND OF THE INVENTION

Diabetic Retinopathy is the leading cause of blindness of adults aged 20-74 years, causing up to 14,000 new cases of blindness each year. 15.7 million Americans, or 8.2% of the adult population, have diabetes, with approximately one-third of these cases undiagnosed. Nearly half of these people will develop some form of detectable diabetic eye disease in their lifetime. Ominously, the incidence of the more common Type 2 diabetes (formerly known as non-insulin-dependent diabetes mellitus (NIDDM) or adult-onset diabetes) is predicted to rise sharply within the next decade, farther increasing the number of Americans at risk for vision loss and blindness. These facts show that diabetic retinopathy is a very serious and pervasive health risk among the American populace. Fortunately, blindness caused by diabetic retinopathy can be successfully prevented, if detected early enough. Strict monitoring and control of blood sugar levels has been shown to delay onset and slow progression of diabetic eye disease. For those who have already developed diabetic retinopathy, laser coagulation treatment has been shown to significantly reduce the risk of blindness. The odds of successful treatment are higher when treatment is administered in the early stages of the disease, further increasing the importance of early detection.

There is no disagreement on the need for regular screening of the diabetic population, but studies indicate that many people at risk still do not get adequate screening for ocular complications of diabetes. One study found that 26% of younger-onset diabetics and 36% of older-onset diabetics had not had an ophthalmic exam, and that 7% of younger-onset and 11% of older-onset diabetics had either never had an eye exam, or had not visited an ophthalmologist within the previous two years. The lack of proper screening is even more severe among the population groups that are at greater risk, such as African Americans or Latinos; groups who are nearly two times more likely than non-Hispanic whites to get diabetes. Characteristics of groups less likely to get the recommended ophthalmic care include low education, low income, shorter duration of diabetes, less severe diabetic retinopathy, no history of ocular problems, inadequate or no health insurance, and youth. Minorities, non-English speakers, those not seeing a diabetes specialist, and non-insulin users are also less likely to get the recommended eye exams. Potential barriers to screening include cost, lack of time, lack of transportation, no insurance coverage for the eye exam, lack of access to a local eye care provider, lack of a referral from the treating physician, lack of awareness about the importance of screening, and lack of understanding of potential risks and benefits.

Telemedicine and TeleOpthalmology

Telemedicine is a method of providing medical care from a remote location electronically via telephone, Internet, satellite, or other electronic means. In a typical telemedicine application, a device known as a "telemedicine peripheral" is used to collect physiological data or images, which are transmitted to an expert at a remote site for analysis. The person who takes the data need not be highly skilled if the peripheral can be made simple enough to use. In some cases, the person using the telemedicine peripheral device may be the patient themselves, as evidenced by the growing market for home care telemedicine monitoring peripherals. Another popular application of telemedicine is a remote consultation facilitated by a videoconference between the patient and the medical caregiver.

Telemedicine has historically been touted as a solution to the problem of access to medical care. Telemedicine is a viable way of addressing the issues of remote location, lack of access to specialty providers, and managed care cost constraints. Telemedicine promises improved access to medical care to diverse groups of people ranging from astronauts and soldiers to rural families and inner city residents. The notion has been around for decades, but the enabling technology is relatively new. Growth has been rapid in the 1990s, but implementation is still low. Some of the barriers to widespread implementation include technical issues such as bandwidth and image compression, licensing issues, malpractice concerns, physician reluctance, confidentiality concerns, and reimbursement issues. The technological barriers are retreating quickly due to advances in the rapidly expanding field of telecommunications. Driven by increasing technological breakthroughs and the pressures of cost-containment, interest in resolving the legal, ethical and reimbursement issues telemedicine continues to build on both a national and local level. Several states have developed their own telemedicine pilot programs, and various branches of the federal government have made a significant investment in telemedicine research and development.

Patient acceptance of telemedicine has been reported under numerous studies to be consistently positive, with overall satisfaction as high as 98.3%. User satisfaction is also positive, eliminating another potential barrier to widespread use. Telemedicine is proving to be a cost-effective way to provide medical care, particularly when used for screening purposes. For example, the Navy determined in a recent study that installation of telemedicine systems on-board ships would be cost effective, saving unnecessary MEDEVACs costing several thousand dollars each. Overall, the outlook is positive for the future growth of telemedicine. Telemedicine has the potential to completely revolutionize the healthcare industry, restructuring nearly every aspect of twenty-first century medicine.

TeleOpthalmology seems particularly well suited to rapid screening for diabetic eye disease. Several studies indicate that non-mydriatic retinal imaging, including digital imaging, is a viable and effective way to screen for diabetic retinopathy. Problems with this method include false positives, which are rare, and poor image quality unsuitable for accurate diagnosis. These problems are not pervasive, and do not outweigh the advantages of this method of screening. The main cause of poor image quality is corneal opacity, which is a problem mainly for older patients. Such patients are far more likely to be under regular ophthalmic care, and are less likely to need this type of screening for this reason.

Currently, ophthalmology systems for telemedicine exist, but their usefulness has been restricted by their high cost, large size, and complexity of use. Even products touted as "hand held" include a tethered connection to a larger base unit (Nidek NM-100 is one such example). These products tend to be multi-functional and are intended for use by ophthalmologists, optometrists, or other highly skilled medical professionals. Their costs range from $12,500-$32,000 or more for complete instruments that are telemedicine-ready, to thousands of dollars for a simple video add-on that is useful only if the physician also possesses a compatible opthalmoscope. Physicians in poor or rural areas are not likely to have the space, funds, or skills necessary to make use of these devices. These instruments are less likely to appeal to other primary care providers as well.

SUMMARY OF THE INVENTION

This invention features a simple, compact, low-cost screening device targeted toward medical practitioners with little or no prior experience with retinal imaging or imaging of the external auditory canal. The market for such devices is likely to grow in size as the shift toward lower-cost medical providers continues, driven by the managed care industry. An aging population, and rapidly growing incidence of diabetes also drive this market. Primary care physicians are called on more frequently to do the work of specialists, and nurse practitioners are taking on more of the duties of doctors, including seeing patients. Doctors will continue to surrender more of their traditional duties to less-skilled staff and will assume more of a care manager and advisory role for their patients. It is important for medical device developers to keep this trend in mind in order to place the proper emphasis on ease of use and simplicity of their devices, especially those intended for use by non-specialists. Since it is clear in the case of diabetic retinopathy screening that the best chance of maximizing the diagnosis of retinal disorders is through screening within the primary care setting, the invention provides for increased access to screening for the populations that need it the most. In rural and underserved areas where the lack of specialists coincides with the lowest rate of screening, highest risk of undetected diabetic eye disease, and the least amount of resources to buy large and expensive equipment, the small, low-cost inventive digital opthalmoscope provides a promising means to decrease the incidence of blindness and vision loss among diabetics.

The inventive handheld, battery-powered device acquires images of the retina. The images can be transmitted from the examination site to an expert reading center via a standard telephone line, cellular link, or Internet connection. An expert consultant can then view the images on a high-resolution color monitor. The images may be compared to previous images stored for that particular patient, or to a library of standard diagnostic images. A diagnostic response may be made back to the referring party within minutes, either by telephone, fax, pager, or e-mail. If evidence of retinal abnormality is seen, the patient may be referred to an ophthalmologist for a complete mydriatic exam and follow-up treatment. For the primary care physician, routine screening of high-risk patients may be offered economically. The periodic monitoring of known diabetic patients will improve their standard of care and reduce medical costs by detecting ocular problems at an early, treatable stage. The device may also be used as part of a routine physical exam, and may be able to identify previously undiagnosed diabetics by means of diabetic retinopathy. Some patients already have detectable diabetic retinopathy by the time a diagnosis of diabetes is made. An eye exam included as part of a routine physical may also allow other eye diseases to be detected earlier and referred to an ophthalmologist, since patients with no perceived visual problems are not as likely to have regular eye exams.

In addition to the telemedicine service, image data can also be output from the inventive device in standard file formats for storage in any personal computer. Data formats can be compatible with emerging Picture Archiving and Communication Systems (PACS) standards such as the Digital hnaging and Communication in Medicine (DICOM) standard, enabling integration with the user's medical management software. Optional color printers may be used to produce hard copy records of the images for inclusion in paper records, to give to the patient, or to provide to another consulting practitioner. The ability to store images is important in order for a healthcare worker to quickly assess disease progression. There is a great opportunity for the advancement of scientific knowledge by having access to larger numbers of retinal images for research purposes.

The inventive device is greatly needed in developing countries where electrical distribution is limited and unreliable. Therefore, cordless operation is important. The inventive device may therefore be supplied with disposable batteries, or a rechargeable battery and charger. Alternatively, other internal power sources such as a fuel cell, or a super-capacitor with a wind-up charger may be used.

An optional, rugged carrying case can be offered for home visits and other mobile applications.

An optional portable or wearable computer may be offered that can store thousands of images or other patient data in mobile applications. The inventive device may communicate with the computer (or another local computer) through any known wired or wireless communications medium, including a cable, a cellular system, a radio frequency link, or an infrared link, for example. For the U.S. and potentially other markets, security features may be incorporated that ensure compliance with the privacy provisions of the Health Insurance Portability and Accountability Act of 1996 (HIPAA). These features may include password protected access to patient data and encryption of certain data.

In addition to screening for diabetic retinopathy, the inventive device has other uses. These include diagnosis of retinal disorders such as hypertensive retinopathy, detached retina, macular adenoma, and retinal blastomas. It may prove useful for detecting retinal damage due to trauma, such as "shaken baby syndrome", and is capable of documenting such injuries by producing images that can be saved to a computer disk. Beyond primary care, the device can be used for mobile retinal exams in locations such as battlefields, disaster areas, ambulances, rescue helicopters, submarines and ships, mobile clinics, third-world countries, and refugee camps. The device can also be used by school nurses, visiting home care nurses, emergency room staff, and in community clinics.

The inventive device is an instrument that makes use of the eye as a unique portal into the human body. The eye provides visual access to the vascular system, offering the potential to perform a range of diagnostic tests and therapies. Emerging photonics technologies enable operation at an array of wavelengths with ever increasing sensitivity and resolution.

In addition to ophthalmic uses, the inventive device is usable for otoscopy, or examination of the 'external auditory canal'—the tunnel that leads from the outer ear (pinna) to the eardrum. Inspection of the eardrum can also provide a lot of information about what is happening within the middle ear— the space within the skull where the hearing and balance mechanisms are situated. In general, parameters such as illumination spectrum, working distance, field of view, resolution, and magnification are very similar for the eye and ear. However, if needed, an accessory lens may be attached to the inventive device that optimizes optical performance for otoscopy.

The inventive device may also have biometric uses. For example, it may be used as a portable retinal scanner to confirm identities in high security facilities, including airports, prisons, and federal facilities. In the military, active service personnel may have their retinas scanned and stored in a central database. The inventive device may then be used for security purposes, as well as for mobile forensics on casualties. For these and other applications, it is useful to incorporate means of indelibly embedding certain data into the images. For example, a global positioning sensor (GPS) may be incorporated into the device so that the global coordinates of the device at the time of image capture are known. Likewise, means of entering the identification (ID) of the user may be incorporated. Such means may include secure data entry or the automated reading of a user ID tag with a barcode reader, RFID receiver, or infrared receiver. Means for indelibly embedding a date stamp, global coordinates, user ID, and other data into images will allow such images to meet higher evidentiary standards in courts of law. "Indelibly" means that the data may not be altered or removed from the image without detection.

Specifications for the inventive device include the following:

1) The field of view should be large enough to gather all the necessary information in one image. Preferred fields of view ranged from 20 to 50 degrees.
2) The image acquisition time of 1/60 second would be sufficient to minimize the image blur caused by non-voluntary movement of the patient's eye, such as micro saccade, and drift and tremor in the user's hand.
3) Market acceptance of the device will be influenced by how the user can bill the procedure to insurance providers. Features may be included in the operating software to assist with billing.
4) Contact between the device and the patient will require frequent cleaning and may result in poor market acceptance. A non-contact imaging system is preferred.
5) The capability to produce red free images is useful to the diagnosis of diabetic retinopathy. Other filters and slits for illumination are not required.
6) The device should make no noise prior to taking the picture as this alerts the patient and causes flinch or blink reactions.
7) +/−10 diopter range of focus adjustment will accommodate about 95% of the population.
8) The device should work in a non-mydriatic mode, i.e., without dilating the patient's pupil.
9) A template may be created on the display for the purpose of achieving the correct image alignment. For example, a circle is displayed, and the user then places the live image of the optic nerve within the circle. This would assist non-professionals in obtaining the correct field of view.
10) For simplicity of design and ease of use, the device should have a fixed field of view. Rather than having optical zoom capability that allows the user to select the field of view, the pictures from the device must have sufficient resolution to allow examining specialists to zoom the image digitally. If the user has concerns about the retina outside of the central field of view, then the camera may be panned and tilted to view different parts of the retina and multiple images recorded. A field of view of 30-50 degrees was chosen in order to keep the size of the device compact. The larger the field of view, the larger the objective lens needs to be, and the larger the entire device becomes.

This invention features a hand-held digital camera for obtaining images of a portion of a patient's body, comprising a hand-held housing that is designed to be placed close to the portion of a patient's body being imaged, a visible light source located within the housing for providing light along an illumination path from the housing aperture to the patient's body, an image sensor located within the housing that detects light returning from the patient's body along an imaging path that passes into the housing aperture, an optical system located within the housing with separate illumination and imaging paths, an external optical aperture common to the illumination and imaging systems, in which the illumination and imaging sub-apertures are wholly contained within the common external aperture, are longitudinally coincident, and are laterally separated and non-overlapping, a digital memory device for storing captured images, an output display carried by the housing, and a means of electronically transmitting stored images.

The camera may further comprise an infrared light source located within the housing that is used instead of a visible light source during alignment and focusing of the image. The camera may further comprise means for automatically adjusting the infrared irradiance. The camera may still further comprise means for automatically setting the visible illuminance based on the optimal infrared irradiance.

The camera may further comprise an internal power source that enables cordless operation. The camera may further comprise means of operating on wind-up or other human-input energy that enables cordless operation.

The field of view of the camera is preferably at least about 30 degrees. The large field of view may be accomplished by using an objective lens with large entrance aperture and high numerical aperture. Preferably, the illumination field exceeds the field of view. The illumination and imaging fields may be combined using a beamsplitter in close proximity to the housing aperture.

The camera may be used to image the fundus of the eye, in which case the illumination path and the imaging path both pass through the pupil plane and are separated in the pupil plane. In this case, the housing portion that contains at least some of the illumination optics may wrap around the subject's cheek in the temporal direction, so that relatively large optics can be placed in proximity with the eye without interfering with the nose or cheek. In order for the camera to be used for both left and right eyes, the housing may define an illumination assembly that is adapted to swivel around the optical axis of the imaging objective lens. Preferably, the images of the illumination and imaging apertures do not overlap at the pupil plane. At the pupil plane, the illumination aperture may be about 1 mm in diameter, and the imaging aperture may be about 2 mm in diameter.

The camera may accomplish at least a plus or minus 10 diopter range of focus adjustment. The camera may further comprise a template on the display to assist the user in aligning the camera with the portion of the patient's body being imaged. The camera may further comprise means for communicating directly with a nearby computer. The camera may further comprise a user-operated image focus. The camera may further comprise a touch screen over the display. The camera may further comprise means to electronically filter one or more wavelengths from the image. The camera may further comprise means to electronically stabilize the image.

A picture-in-picture may simultaneously display the whole field and a segment of the field at higher magnification. In this case, the camera may further comprise means for the user to select a segment of the field for displaying in a picture-in-picture. The camera may further comprise a large area image sensor to limit optical magnification and thereby reduce device size. The camera may further comprise means for automatically adjusting the visible illuminance. The camera may further comprise means for projecting stored images. The camera may further comprise templates on the touch screen to aid in entering commands or data.

The camera may further comprise a barcode reader for automatically capturing data from a barcode, an RFID receiver for automatically capturing data from an RFID transmitting device, or an infrared receiver for automatically capturing data from an infrared transmitting device. The camera may further comprise means for automatically focusing the image.

The camera may further comprise means for automatically capturing the image when one or more predetermined conditions are satisfied, in which case it may still further comprise means for automatically capturing multiple images in rapid sequence. The camera may further comprise means for automatically capturing multiple images in rapid sequence, in which case it may still further comprise electronic means for automatically selecting captured images that satisfy one or more predefined conditions.

The camera may further comprise an easily transportable headrest for the patient, in which case there may be replaceable parts or covers for parts of the camera that contact the patient. The camera may further comprise a mechanism for mechanically stabilizing the camera relative to the patient. The camera may further comprise means for protecting the privacy of patient data with at least one of password protecting images and encrypting images. The camera may further comprise one or more polarizers in the imaging path to decrease specular reflections from the patient.

The visible light source may comprise a broadband light source, and the camera further comprising means for filtering the light from the source, to illuminate the patient with different spectral bands. The camera may further comprise a global positioning sensor. The camera may further comprise means for indelibly embedding evidentiary data into images. The camera may be used to image the external auditory canal.

Also featured is a method that allows a remotely-located expert to interpret an image of a portion of a patient's body, comprising providing a hand-held camera comprising a hand-held housing that is adapted to be placed close to the portion of a patient's body being imaged, a visible light source located within the housing for providing light along an illumination path from the housing aperture to the patient's body, an image sensor located within the housing that detects light returning from the patient's body along an imaging path into the housing aperture, an output display carried by the housing, an optical system located within the housing and that separates the illumination and imaging paths, an external optical aperture common to the illumination and imaging systems, in which the illumination and imaging sub-apertures are wholly contained within the common external aperture, are longitudinally coincident, and are laterally separated and non-overlapping, a digital memory device for storing captured images, an output display carried by the housing, and a means of electronically transmitting stored images. The camera is used to capture an image of the portion of a patient's body being imaged. A computer with a display device is provided at a remote location. The captured image is transmitted over a network to the remote computer, for interpretation by an expert. Application software may be provided in the computer to facilitate the review, interpretation, and archiving of images.

BRIEF DESCRIPTION OF THE DRAWINGS

Other objects, features and advantages will occur to those skilled in the art from the following description of the preferred embodiments and the accompanying drawings in which.

DESCRIPTION OF THE PREFERRED EMBODIMENTS OF THE INVENTION

Figure 1:
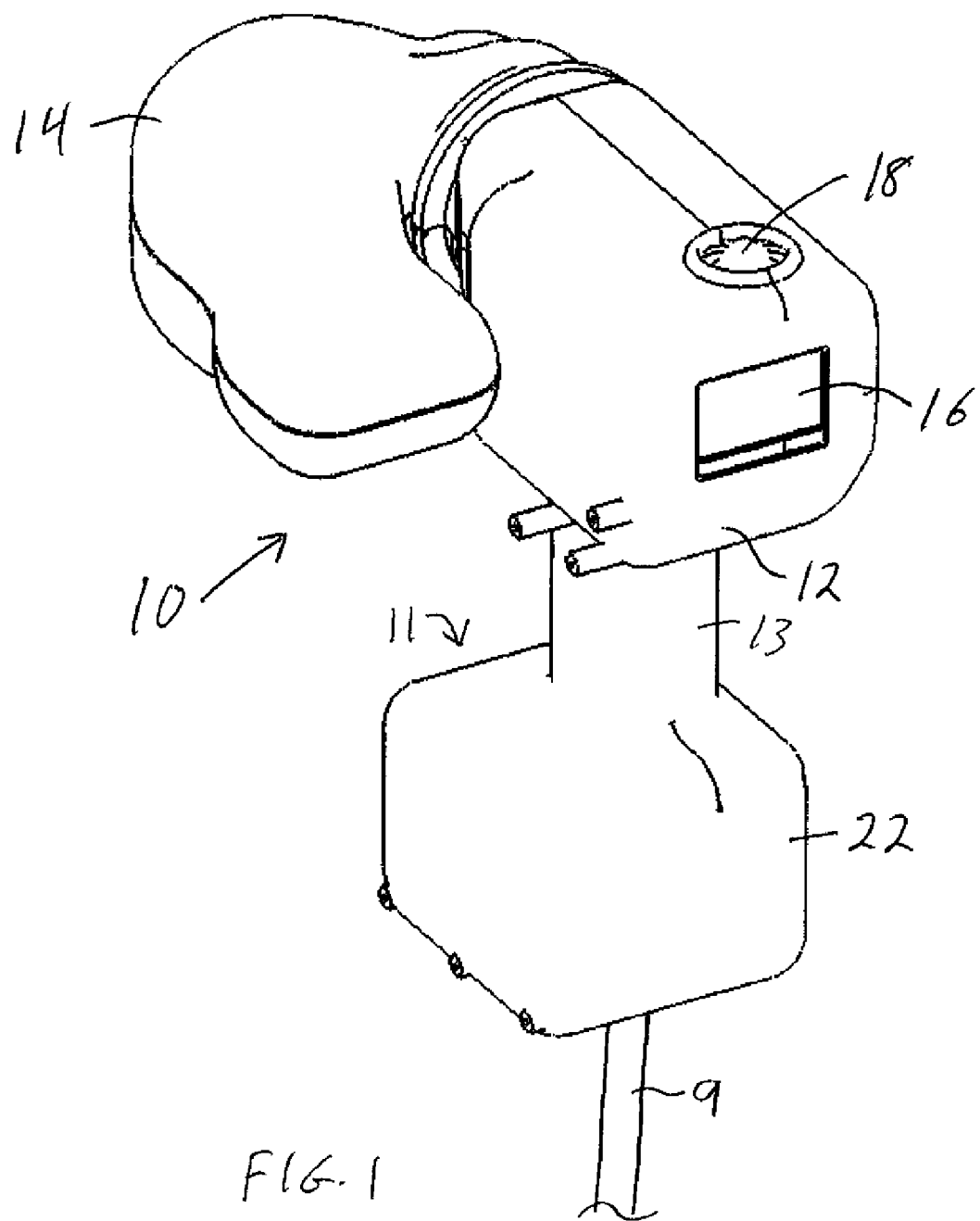
FIG. 1 is a schematic rear view of the preferred embodiment of the portable digital retinal camera of this invention.
Figure 2:
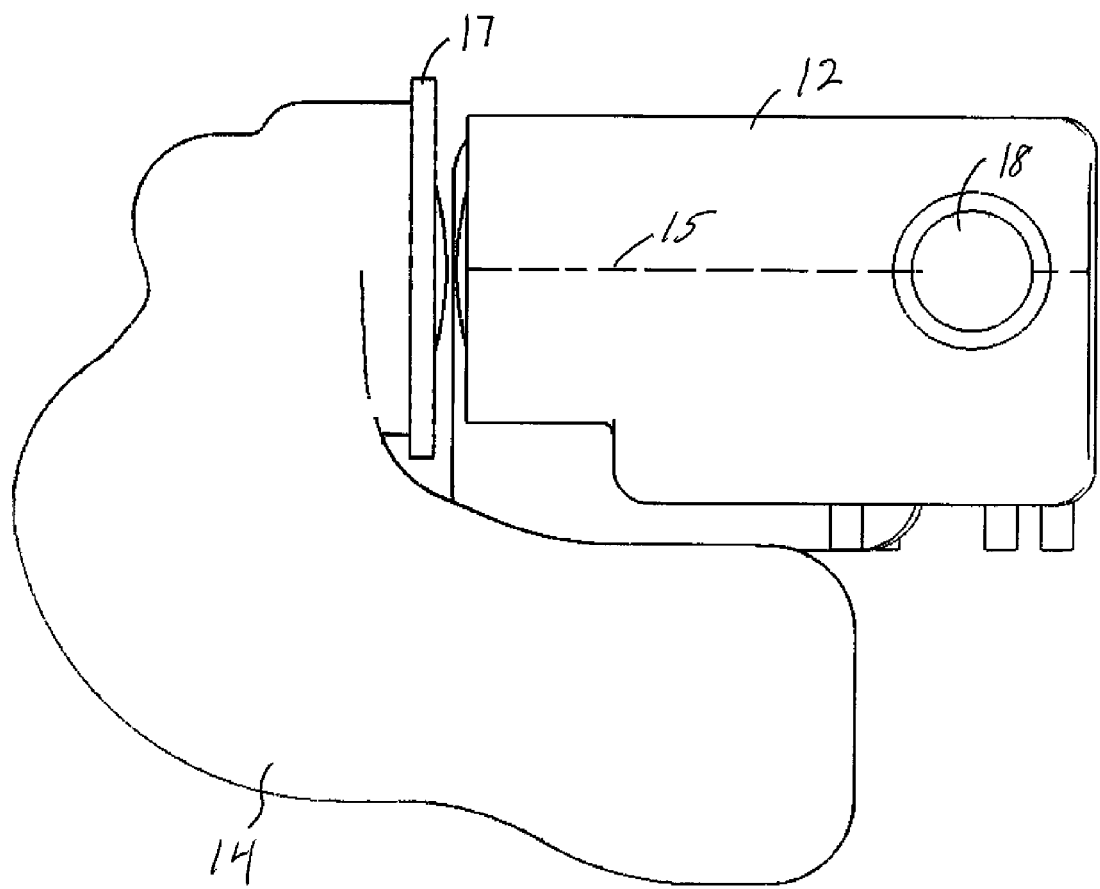
FIG. 2 is a top view of the camera of FIG. 1.
Figure 3:
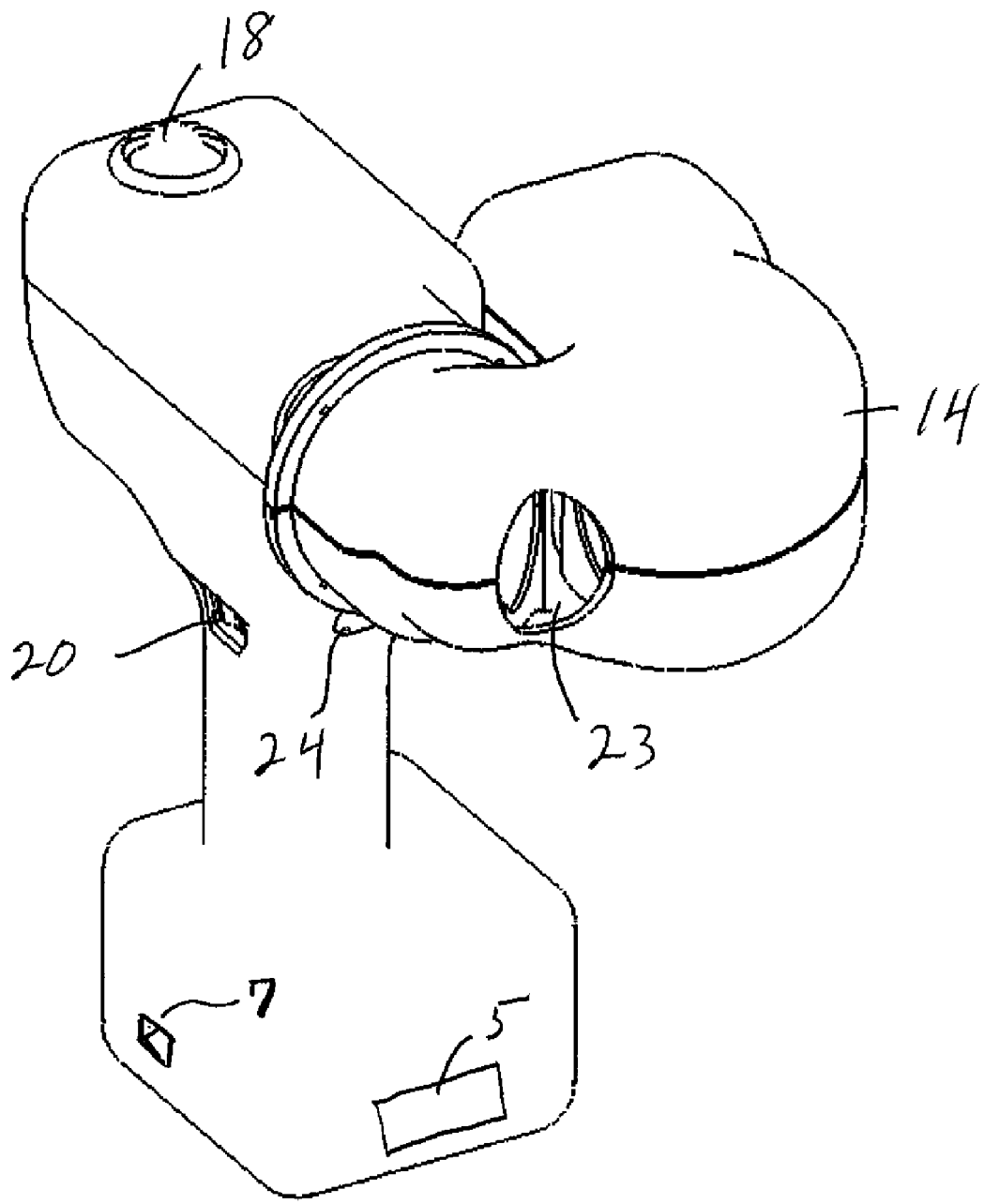
FIG. 3 is a front view of the camera of FIG. 1.

The preferred embodiment of the inventive device, shown in FIGS. 1-7, offers the following features and benefits:

Handheld device for maximum portability.

Overall size of about 7W"×9L"×10H" (180×230×250 mm).

Overall weight of about 2 lbs (1 kg).

Powered by a rechargeable battery with a small wall charger.

Designed for non-mydriatic use (no pupil dilating drugs required).

40° Field of View.

A near infrared light source used for aiming and focusing. This prevents pupil constriction that is caused by exposure to visible light.

When the user sees that an image is lined up and focused, a trigger is squeezed. This initiates a flash and a white light image is automatically captured.

The captured image is automatically presented on the screen, and then the camera is ready for the next shot.

Zoom and pan features let the user view the image on a small screen to determine whether image quality is acceptable.

Images are stored on removable digital storage media such as "memory sticks".

Images are read out to a local computer over a USB 2.0 or other serial communications port.

The sensor for the device can be any available sensor with an appropriate size and resolution. The preferred embodiment is a large sensor with high resolution (2-4 megapixels). The large sensor is preferred in order to minimize the difference in area between the image produced by the objective lens and the area of the sensor. Such sensors require a small change in magnification from the imaging optics. This results in a shorter optical path length and a more compact device.

Red free images are often desired in retinal imaging in order to improve the contrast of certain anatomical features. Red free images may be produced by electronically subtracting the red color information after capturing an image. This eliminates the need for a physical red filter in the camera. This saves the cost of the filter and the parts required to move it in and out of the optical path, reduces system complexity, and increases the optical transmission of the system. A technique for subtracting red may also prove clinically useful to subtract other colors when reviewing the images.

The illumination level setting of the IR LED may be used to determine the white flash energy automatically. This eliminates the need for a manual adjustment for flash energy, again simplifying the system, improving ease of use, and reducing cost.

The optical system resolution of the preferred embodiment was matched to the resolution of the chosen image sensor. Once the field of view and the sensor were determined, the magnification of the optical system was determined. To calculate the field of view inside the eye, the Zemax optical model developed by Robeen Webb of Schepens Eye Research Institute and Wellman Laboratories of Photomedicine at Massachusetts General Hospital was used.

From this model, the dimensions of the retina observed by a 30-degree field of view can be determined. The vertical dimension of the CCD is then divided by the retina dimension. The value obtained is the magnification of the system. In this case the magnification is 0.52×.

The illumination system of the preferred embodiment is based on the Gullstrand principle, which is also the method used by many ophthalmic instruments. The purpose of this type of illumination is to provide an image free of reflected light from the cornea. The principle involves separating the illumination and imaging paths in the patient's pupil plane. The illumination will pass through an aperture in the camera that is imaged onto the patient's pupil. The imaging optics will also pass through a separate aperture in the camera, which is imaged onto a different part of the pupil plane. As long as the images of both of these apertures do not overlap then the reflections from the cornea will not be imaged on the sensor.

To accomplish this separation and allow the device to work without dilating the pupil, the images of the aperture need to be small and closely spaced. At the pupil plane, the device images through a 2 mm diameter aperture, and the illumination passes through a 1 mm diameter aperture. This allows the device to work on pupils as small as 3 mm in diameter.

One optical design incorporates a commercial eyepiece to produce an aerial image of the retina. This aerial image is relayed to the image sensor of the digital camera using a Steinheil triplet. The conjugates of the triplet are arranged with the appropriate magnification to image the 30-degree field on the sensor's area. The triplet is the focus mechanism and is moved to compensate for the patient refractive errors. A 28 mm RKE eyepiece from Edmund Scientific was used as an objective lens in this design. This is an inexpensive eyepiece that offers good optical performance and has a large eye relief. Eye relief is the distance from the lens to the pupil of the observer. In this application, the observer is the patient, so this eyepiece is being used as an objective lens. If the eye relief is too small, positioning the device near the patient will become difficult or infeasible, and the patient may be uncomfortable.

With this design, the illumination requirements of the system can be determined. The device uses a Koehler illuminator, where the source is imaged onto the aperture of the system, in this case the pupil of the eye. The efficiency of the illumination optics is then determined, which allows the calculation of the amount of optical power entering the eye. The system is designed so that the converging bundle of rays traveling toward the pupil subtends an angle larger than the field of view. The image of the source on the pupil will then diverge as it enters the eye and evenly illuminate the field of view.

The retina is modeled as a diffuse reflector where light hitting a spot is reflected in all directions. The reflectivity of the retina as well as the transmission of the lens and cornea are also considered. The amount of light gathered by the imaging optical system can then be calculated. All this information is combined into one equation to determine the amount of light from the source that strikes the detector.

$$P_{DETECTOR} = P_{SOURCE}(5.17 \times 10^{-5}) \qquad (1)$$

To determine the power necessary on the camera, the ISO equivalent sensitivity was converted to optical energy. The following formula relates the ISO equivalent to lux and exposure time.

$$ISO = \frac{78}{\text{lux} \times \text{time}} \qquad (2)$$

For an illumination wavelength of 550 nm the following conversion factor can be used.

$$680 \text{ lux} = 680 \frac{\text{lumens}}{\text{m}^2} = 1 \frac{\text{watt}}{\text{m}^2} \qquad (3)$$

The dimensions of the camera sensor are 8.1×6.6 mm. The duration of the camera's flash was set to 300 microseconds. This combined with the equations 2 and 3 yields the relationship between the ISO equivalence and the optical energy. For ISO100, $$N(lux) = \frac{78}{100 \times (3.0 \times 10^{-4})} = 2600 \text{ lux}$$

$$2600 \text{ lux}\left(\frac{1 \text{ watt/m}^2}{680 \text{ lux}}\right)(5.3 \times 10^{-5} \text{ m}^2) = 0.2 \text{ mW}$$

This result is substituted into equation 1 and solved for the source power required.

$$P_D = P_S(5.17 \times 10^{-5})$$

$$P_S = \frac{0.2 \text{ mW}}{5.17 \times 10^{-5}} = 3.9 \text{ W}$$

The required optical energy is a more useful measure of the flash performance. A watt is equal to a joule per second, so the power times the flash duration yields the required energy in joules.

$$3.9 \text{ W}(3.0 \times 10^{-4} \text{ sec}) = 1.17 \text{ mJ}$$

The final result predicts that a flash of 1.17 mJ is needed to saturate the sensor at an ISO setting of 100.

To verify that this level of illumination is permitted in the eye, the Maximum Permissible Exposure (MPE) defined by ANSI Z136.1-2000, American National Standard for Safe use of Lasers, was calculated. The standard classifies sources as small or extended based on the angle they subtend from the pupil. The present illumination system subtends a total angle of 35 degrees or 0.61 radians, which is characterized as an extended source. The standard further specifies exposures by time duration, and the flash falls into the 18 microsecond to 0.7 second range. The following equation is used to calculate the MPE for visible light at these conditions.

$$MPE\left(\frac{J}{cm^2}\right) = 1.8 C_E t^{0.75} \times 10^{-3}$$

where, t=exposure time in seconds=30 microseconds
$C_E$=correction factor for angle subtended=2480 (for 610 mrad)

The MPE is then, $$MPE\left(\frac{J}{cm^2}\right) =$$

$$1.8 C_E t^{0.75} \times 10^{-3} = 1.8 \times 2480 \times (3.0 \times 10^{-4})^{0.75} \times 10^{-3} = 10.2 \, \frac{mJ}{cm^2}$$

Finally we multiply this value by the illuminated area of the retina to yield:

$$MPE(J) = 10.2 \, \frac{mJ}{cm^2}(.91 \text{ cm}^2) = 9.3 \text{ mJ}$$

This result indicates that the 1.17 mJ predicted saturation level of the device is within safe limits. The calculation of the illumination requirements was also performed assuming ISO100. The camera can be set to ISO 400, which would lower the required illumination, by a factor of four.

Hand-held digital retinal camera 10 according to this invention, FIGS. 1-7, includes housing 11 that defines upper portion 12, handle portion 13 and lower portion 22. Active elements shown in FIGS. 1-3 include display 16, function selection switch 18, focus adjustment knob 20, and focus/capture button 24. Swiveling illumination housing section 14 can be swiveled 180 degrees about axis 15, from one side of upper housing section to the other, through coupling member 17. This allows the camera to be placed very close to the eye without the patient's nose and cheek area interfering with it.

Aperture 23 is the outlet for camera focus energy (preferably in the IR) and flash energy, as well as the input for reflected light that is captured by the camera CCD for the image. Camera support such as single pole 9 may be used to stabilize the camera. Data port 7 (e.g. a USB port) may be included to allow the camera to communicate with a local computer. Data capture device 5 (e.g. a bar code reader, an RFID receiver or an IR receiver) can be used to capture and input patient-related data.

Figure 4:
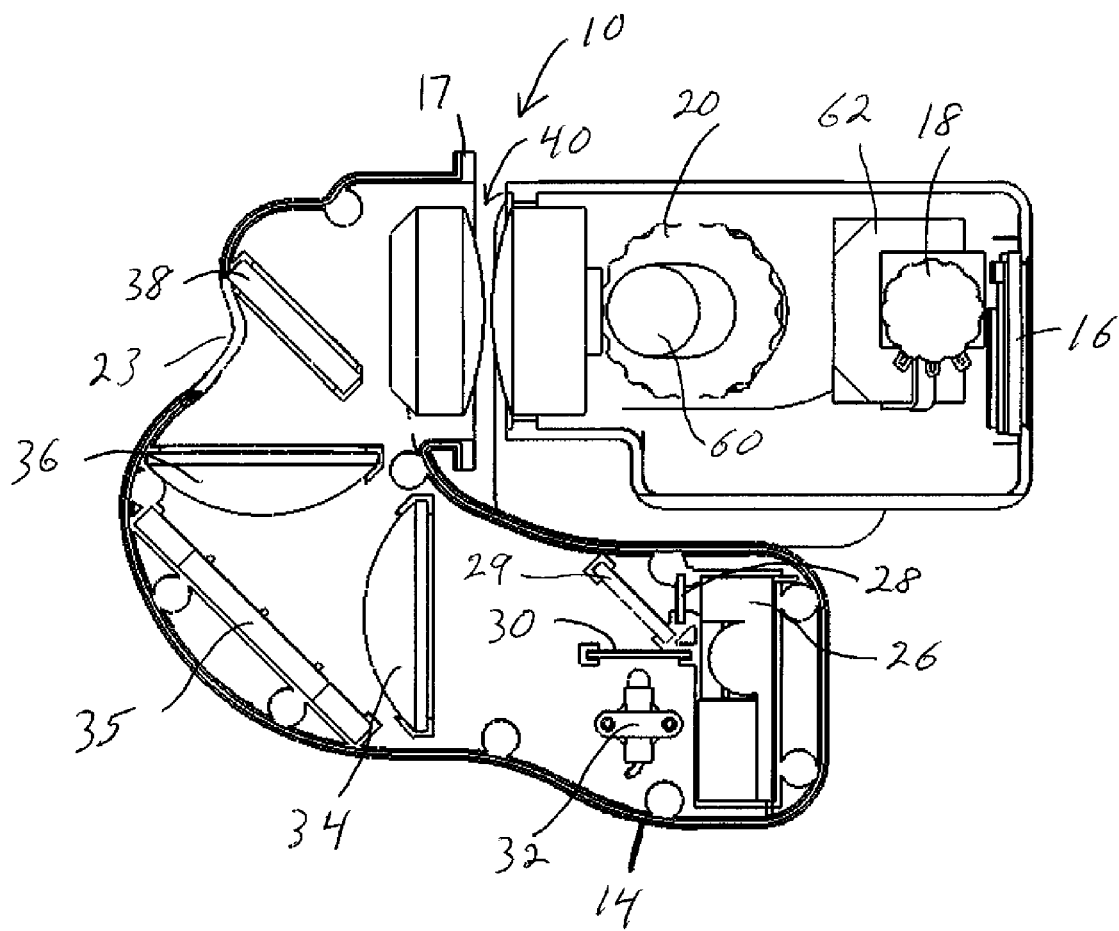
FIG. 4 is a cross-sectional view of the camera of FIG. 1.
Figure 5A:
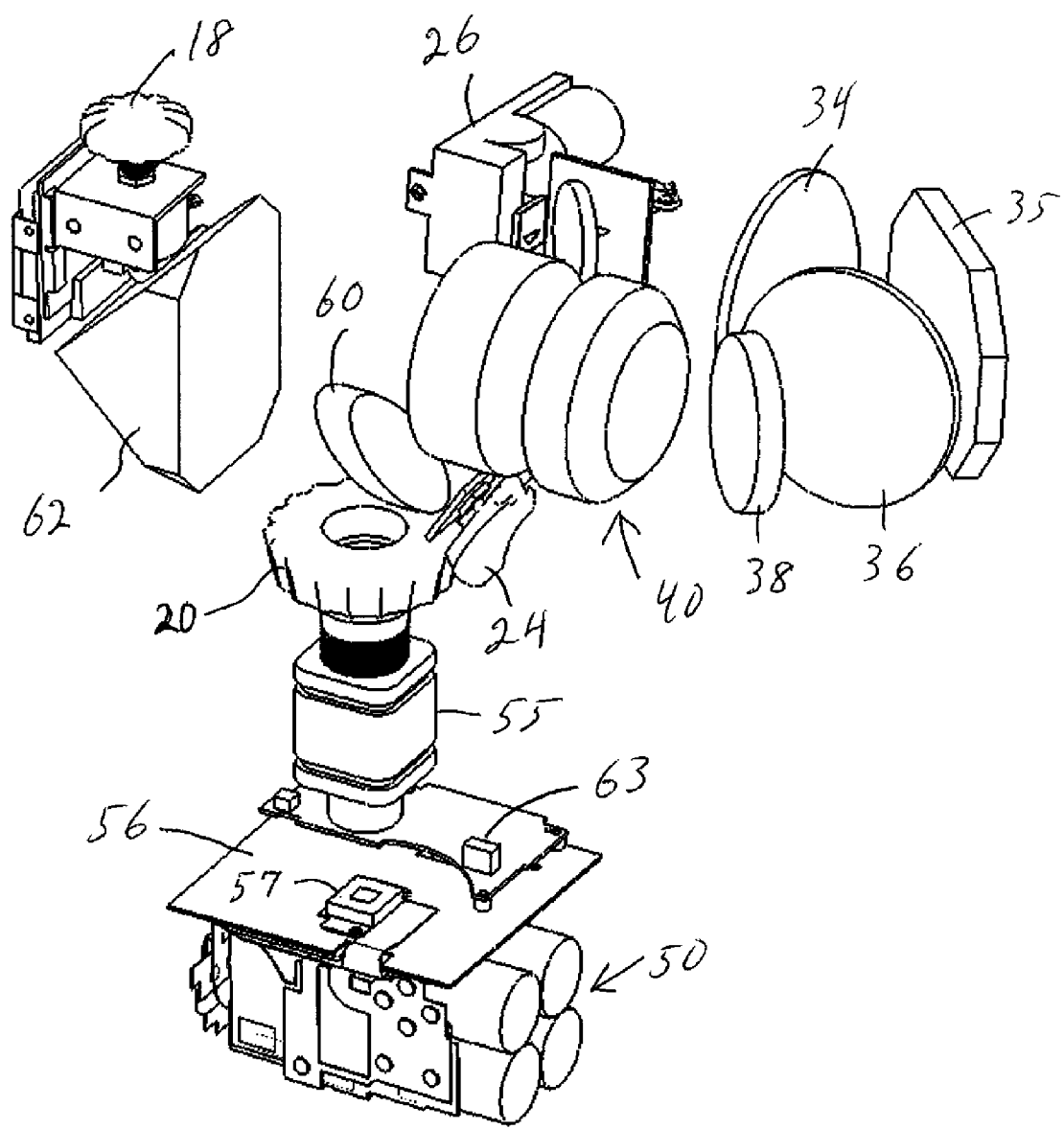
FIG. 5A is a schematic exploded view of the camera of FIG. 1.
Figure 5B:
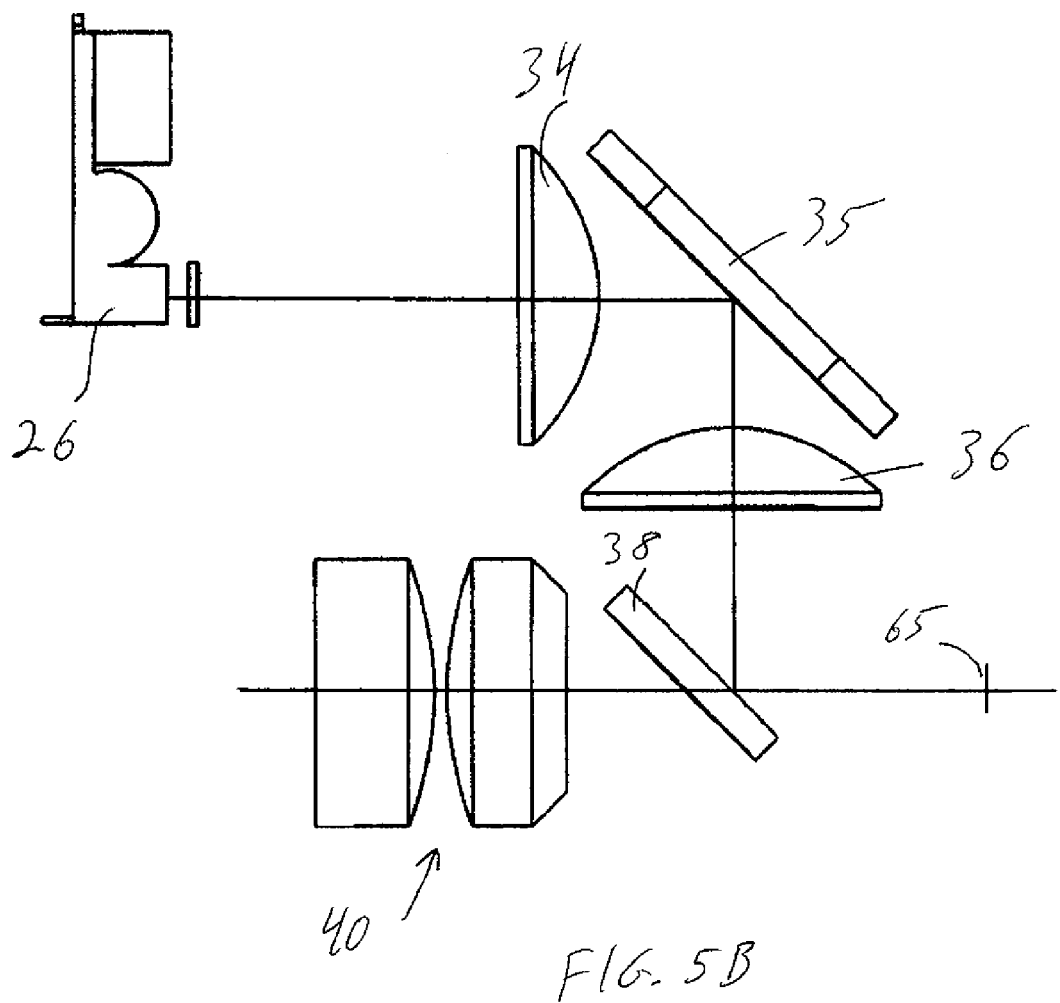
FIG. 5B schematically depicts the illumination and imaging paths and the external optical aperture, and FIG. 5C schematically depicts the separation of the illumination and imaging sub-apertures in this external optical aperture, as accomplished by the preferred embodiment of the invention.
Figure 5:
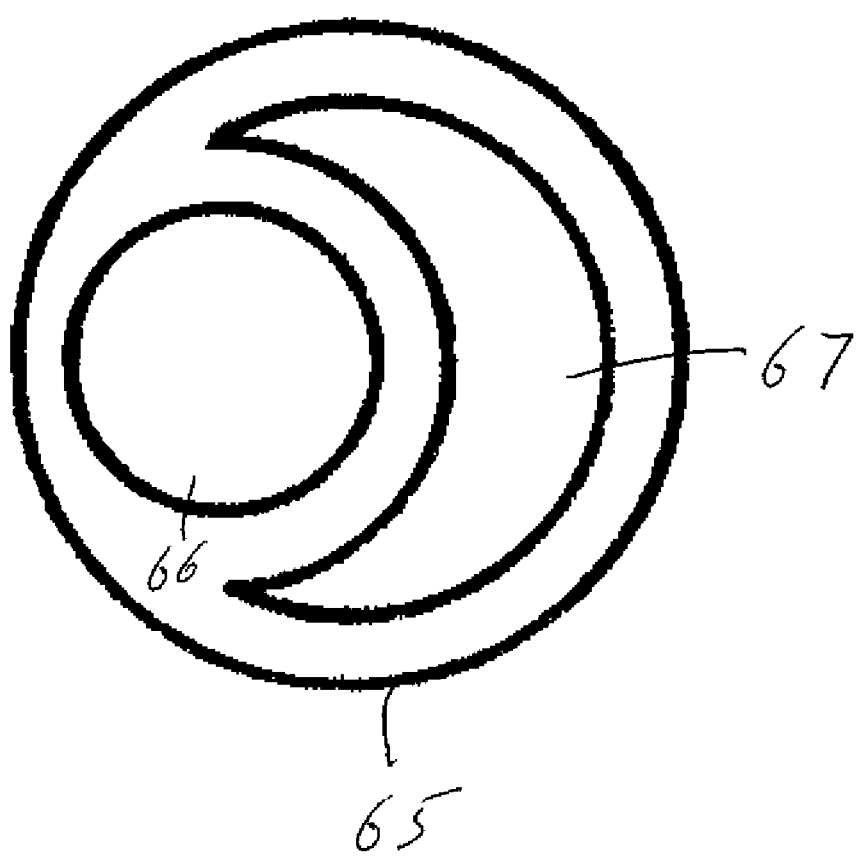

FIGS. 4 and 5A show the active elements of the preferred embodiment. All of the focus and illumination optics are carried by swiveling housing section 14, and include IR LED 32, white light flash unit 26, optical filter 28, hot mirror 29, illumination aperture 30, lenses 34 and 36, mirror 35, and beamsplitter 38. The imaging optics include objective lenses 40, prism 62, turning mirror 60, focusing lenses 55, and an image sensor 57 carried on printed circuit board 56. Batteries 50 provide power to the device. Focusing wheel 20 engages lenses 55. The processor, memory and other electronics are on the circuit boards located in housing power portion 22; one board 56 is called out in FIG. 5. Also shown is an optional GPS device 63. FIG. 5B schematically depicts the illumination and imaging paths in order to identify external optical aperture 65 of the invention, shown in more detail in FIG. 5C, through which illumination sub-aperture 67 and imaging sub-aperture 66 pass such that they are wholly contained within aperture 65, are longitudinally coincident, and are laterally separated and non-overlapping.

Figure 6:
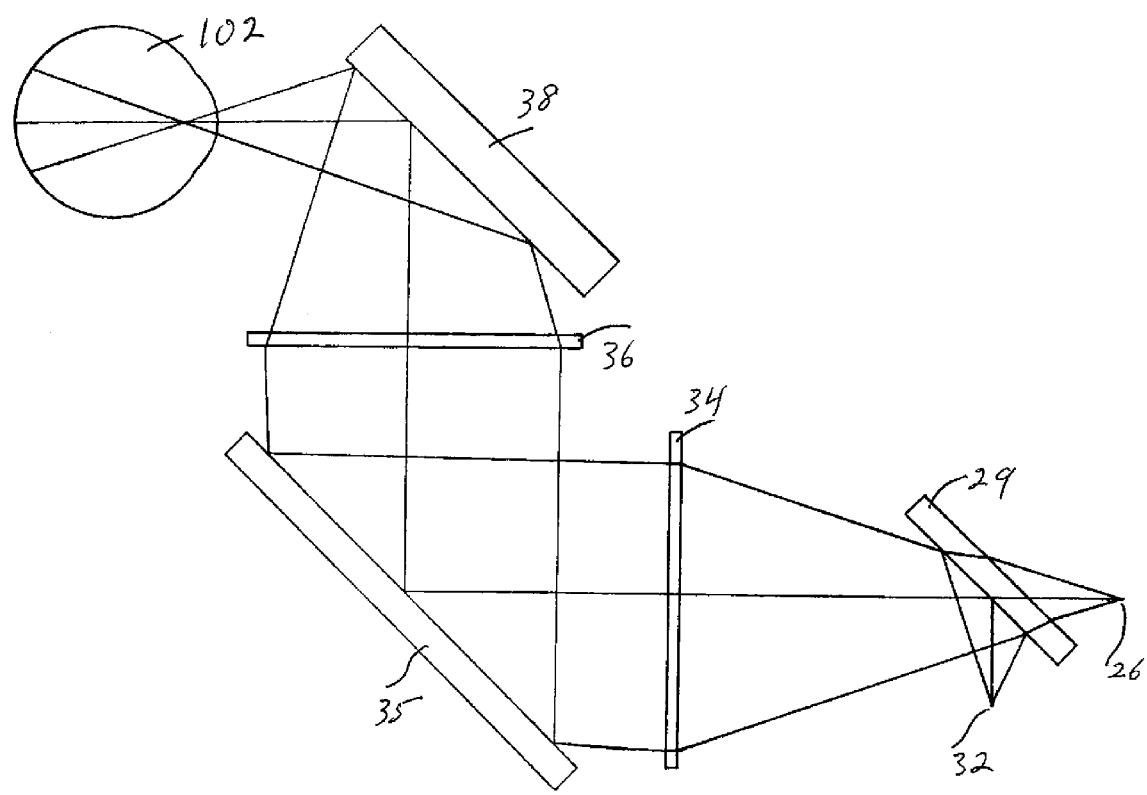
FIG. 6 shows a beamsplitter-based illumination system for the preferred embodiment of the invention.
Figure 7:
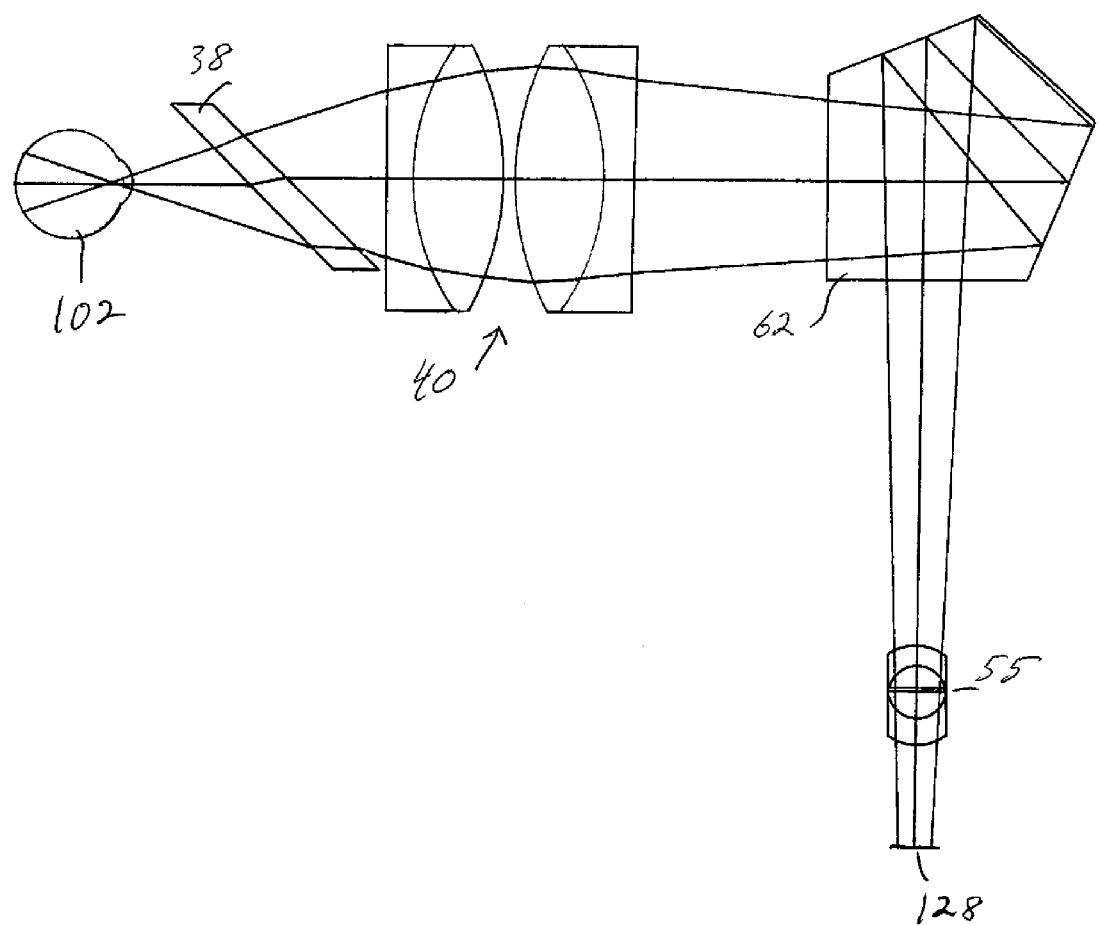
FIG. 7 shows the optical model of the imaging system for the preferred embodiment of the invention.

The preferred embodiment of the illumination system of the invention, FIG. 6, employs a partially reflective mirror (beamsplitter) 38 positioned in front of the objective lens (not shown in FIG. 6). In order to accomplish this, the eye relief needed to be increased so the mirror is further away from the patient's eye. A 55 mm Plossl eyepiece made by Televue (Suffern, N.Y.) can serve as an objective lens to accomplish this. This eyepiece is significantly larger than the RKE used in another design, and has a proportionately larger eye relief. FIG. 7 shows the optical model of the imaging system. Since the back focal length of the Plossl eyepiece is also longer, a penta prism 62 was used to bend the optical path down the handle of the device to image plane 128 in order to keep the system compact.

The illumination system consists of two lenses, 34, 36, to form a condenser system with unit magnification. These lenses may be of the Fresnel type, thick molded condensing lenses of plastic or glass, or thick ground and polished glass condensing lenses. Since the camera should work without dilating the pupil, in the preferred embodiment an infrared (IR) source 32 is used during the alignment and focusing of the image. IR light will not cause pupil constriction, but the camera is still sensitive to the light from the IR source. The two illumination sources may be combined using a hot mirror 29, which has high reflectivity to IR and high transmission to visible light. This entire illumination path can mechanically revolve around the eyepiece so that it can extend to the side of the patient's head away from the nose.

An alternative to using an infrared source for alignment and focusing is to use an image sensor with very high sensitivity. Alignment and focusing may then be accomplished with low level visible light. A further alternative is to align the instrument to the eye using only ambient light, and then rapidly acquire a series of flash images. During this series, focus and exposure are automatically optimized. Software routines are then used to automatically select and display the optimal image(s). Yet another alternative is to use a single broad band continuous or pulsed light source 26, along with filters that accomplish the desired wavelength band at the desired time (e.g. NIR light for focusing and white light for imaging). This can be accomplished by replacing IR LED 32, and hot mirror 29 with a filter wheel or the like.

Figure 8:
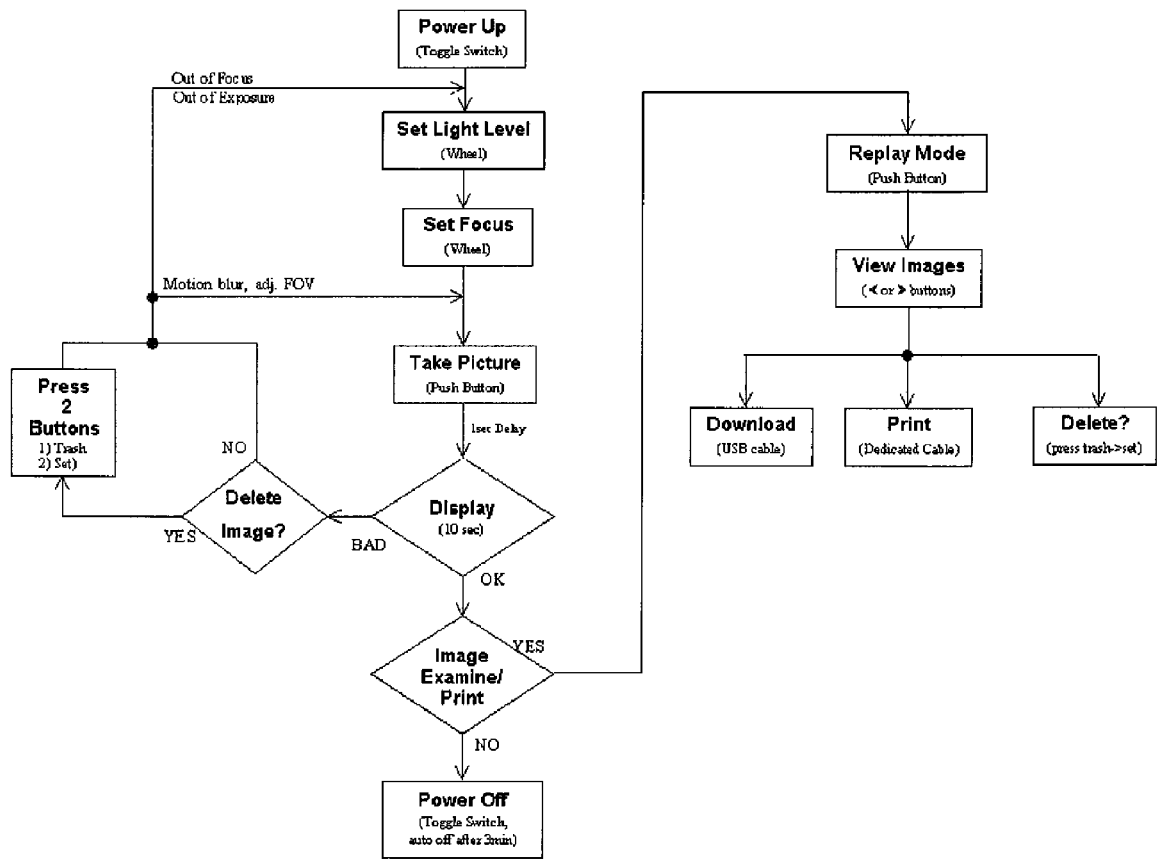
FIG. 8 is a flow chart detailing the basic usage methodology of the inventive camera, for the invention.
Figure 9:
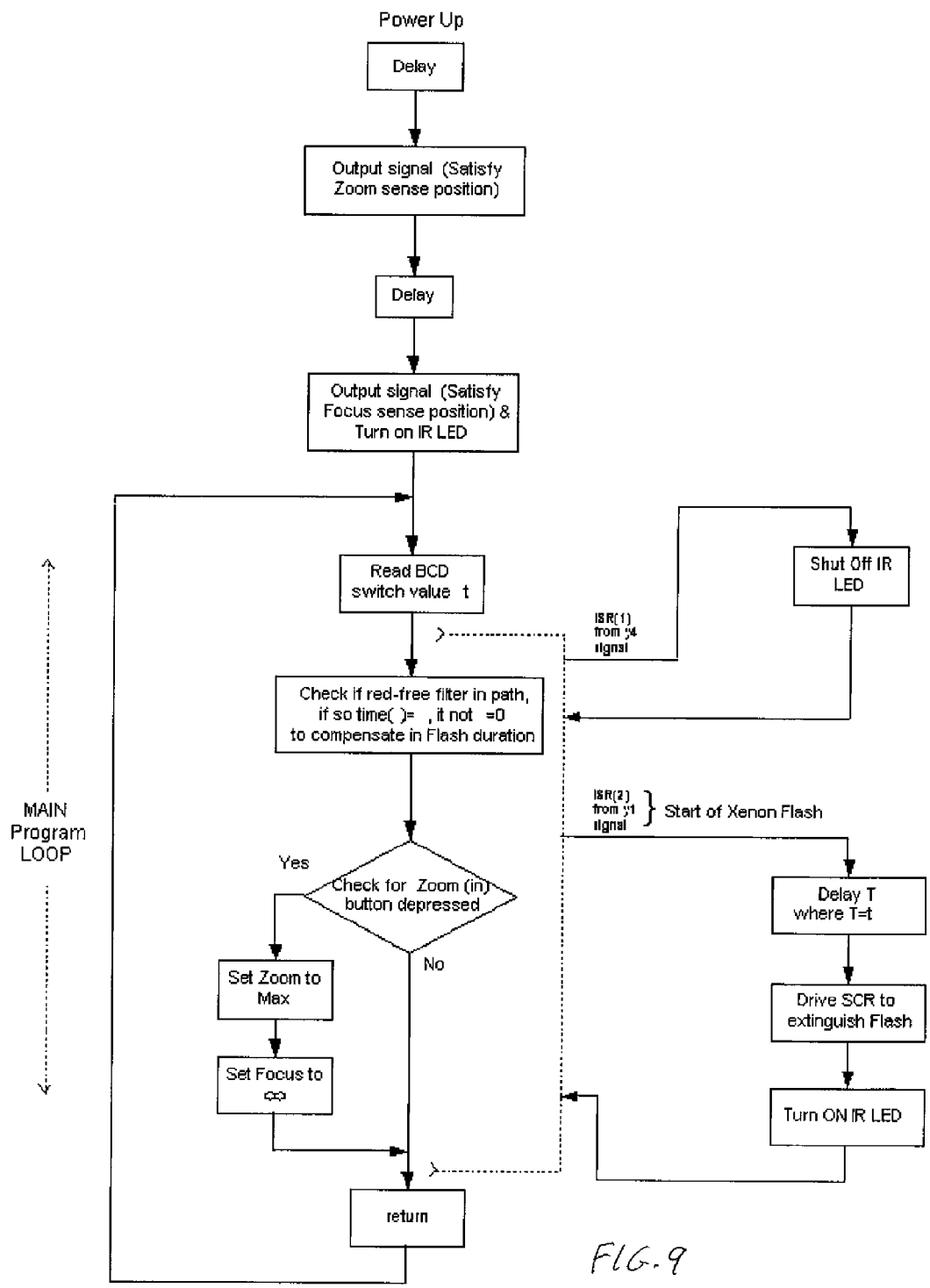
FIG. 9 is a flow chart detailing the flash control and lens positioning for the preferred embodiment of the invention.

Another piece of the product specification is the usage flowchart, FIG. 8. This flow chart documents a minimum set of operations required to obtain retinal images. The flow chart represents an easy and intuitive manner in which to use the camera. FIG. 9 is a logic diagram for controlling the flash. This was the basis for the design of an electronic circuit to perform this function.

Polarizers may be used to attenuate back reflections. A circular polarizer can be placed between the Fresnel lens 36 and the beamsplitter 38. This causes the illumination to have circular polarization as it travels out of the system. Any specular reflections from the cornea will reverse their polarization, while the light reflected diffusely by the retina will have random polarization. As the light travels back through the system toward the sensor, a second polarizer located in the imaging path will extinguish the specular reflection from the cornea, but will transmit that portion of the light from the retina that has the correct polarization. Another option would be to coat an optic in the illumination path, such as beamsplitter 38, with an appropriate polarizer.

Significant weight reduction can be achieved by designing a plastic aspheric lens as the objective lens of device. The penta prism can also be replaced with two mirrors, which will reduce the total glass volume by 80-90%. The fabrication tolerances of plastic lenses are within the system requirements.

Most retinal imaging is done with fundus cameras. These cameras are large, stable, table-top devices, typically with a joystick to provide a fine alignment of the objective lens to the eye. Chin and forehead rests stabilize the patient's head relative to the camera. The patient's eyes are generally dilated to greatly increase the pupil size. This makes it easier to pass the camera's illumination, as well as the return image.

The inventive device should be as easy to use as a consumer-type point-and-shoot camera. However, capturing images of the retina with a handheld device presents some ergonomic challenges. The patient's head is not stabilized. The orientation of the camera relative to the patient's eye is random. The most challenging aspect though, is that images are captured without dilating the eye.

Figure 11:
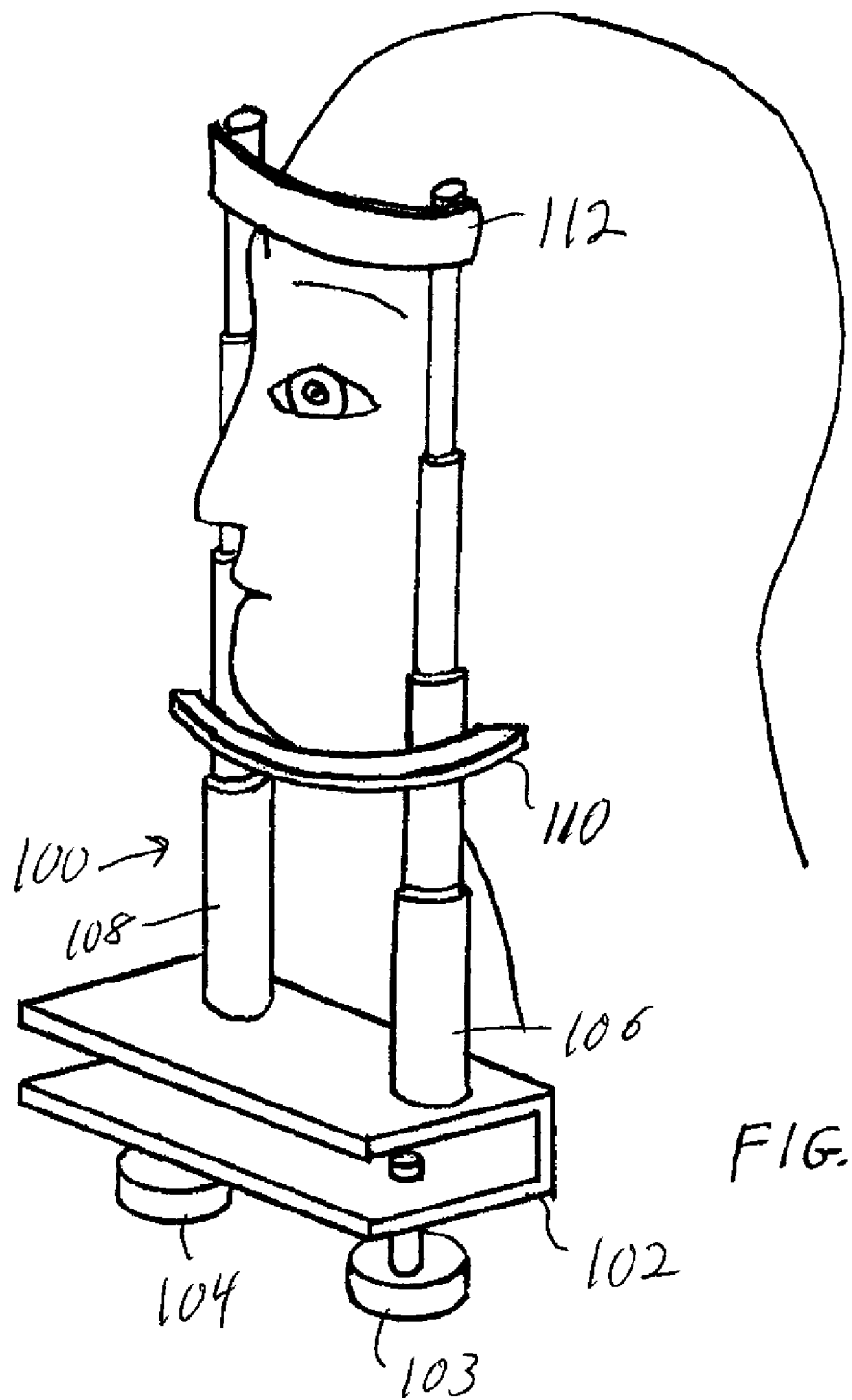
FIG. 11 shows an embodiment of a portable patient head rest for the invention.
Figure 12:
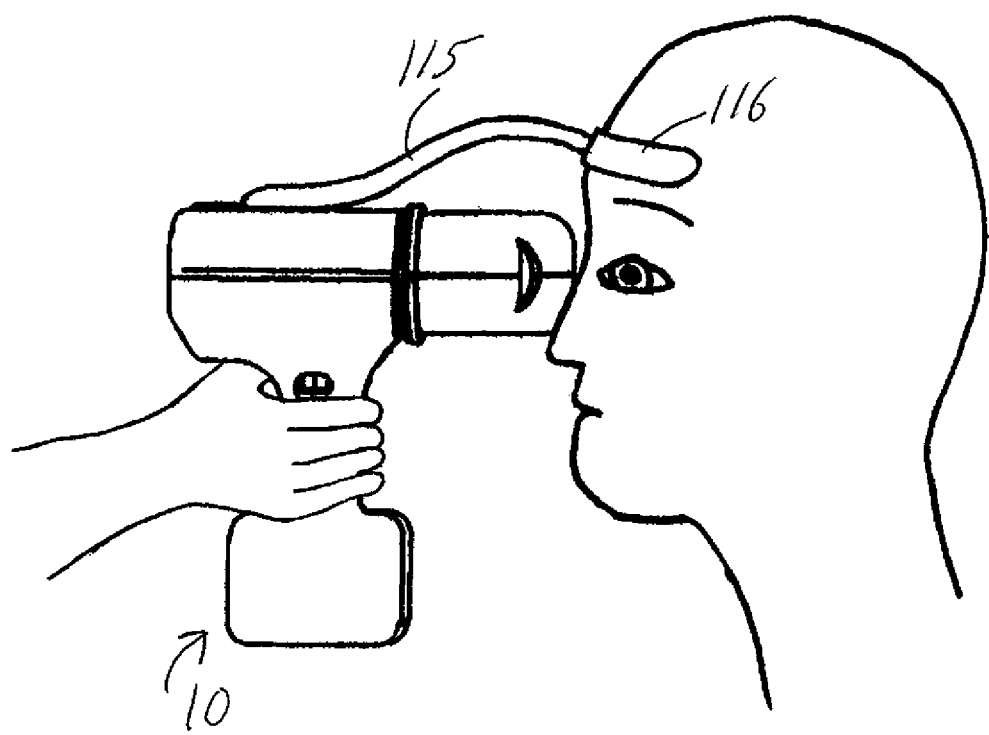
FIG. 12 shows an embodiment of a mechanical stabilizer that aids in the alignment of the camera with the body part, for the invention.

To address the stabilization issue, some opthalmoscopes have a rubber boot that contacts the eye socket. Many patients object to being touched around the eye, especially if the thing contacting them is not sterile. Further, infections such as conjuctivitis may be transmitted from one patient to another in this manner. These problems can be avoided with a portable device such as a lightweight table stand 100, FIG. 11, that supports the patient's chin and forehead, and then collapses into a small package for transport. Stand 100 includes base 102 with table edge clamps 103 and 104, telescoping vertical structural members 106 and 108, chin rest 110 and forehead rest 112. Another version is a telescoping staff 9, FIG. 1, that rests on the ground; the other end supports the camera. The height of the staff is adjusted for a sitting or standing patient. Alternatively, the stabilization device may be a flexible arm 115, FIG. 12, that is attached to the camera 10. Soft pad 116 at the distal end of arm 115 is pressed against the forehead. Flexible arm 115 allows alignment of the camera, but in a more stabilized way. For an approach that includes patient contact, disposable or peel-off covers may be used at the point(s) of patient contact to provide an infection barrier between the patient and the hardware.

To approach the point-and-shoot ideal, the camera controls should be as few as possible, and intuitive to use. This means superior layout of the controls, as well as tactile, audible, and/or visual feedback on control functions. The total number of user commands should be low. Functions may include power on/off, IR illumination intensity, white flash illumination energy (but see below), focus, and picture capture. However, even these controls may be eliminated by automating these functions.

In the preferred embodiment, a small display is used in order to minimize the size of the device. However, manual focusing of the camera in the eye is difficult due to the limited resolution of small displays. Accurate focusing may only be achieved by zooming in the display in order to see the details on the retina. Further, in order to ensure correct alignment of the camera with the eye, the entire field of view must be visible. This conflict between the requirements of focusing and alignment may be eliminated with a high resolution display. However, a high resolution display consumes more power, thus reducing battery life. It is also larger and may make the device too bulky. Therefore, the device may alternatively incorporate a picture-in-picture (PIP) display concept using available, low to medium resolution displays. This means that the display will simultaneously show both the whole field view and a close-up detail in a box. The whole field view can be used to ensure that the camera is properly aligned with the pupil of the eye, and that the illumination is even. The close-up PIP will show the center (or some other part) of the field at high magnification for focusing.

The controls for adjusting illumination intensity, focus, and image capture are integrated into the handle of the device. They are ergonomically placed so that at least the $5^{th}$ to $95^{th}$ percentile males and females, both left- and right-handed, can comfortably use the device. The design is in accordance with Anthropometric standards. To avoid language barriers, all controls are labeled with international symbols instead of linguistic markings.

Figure 10:
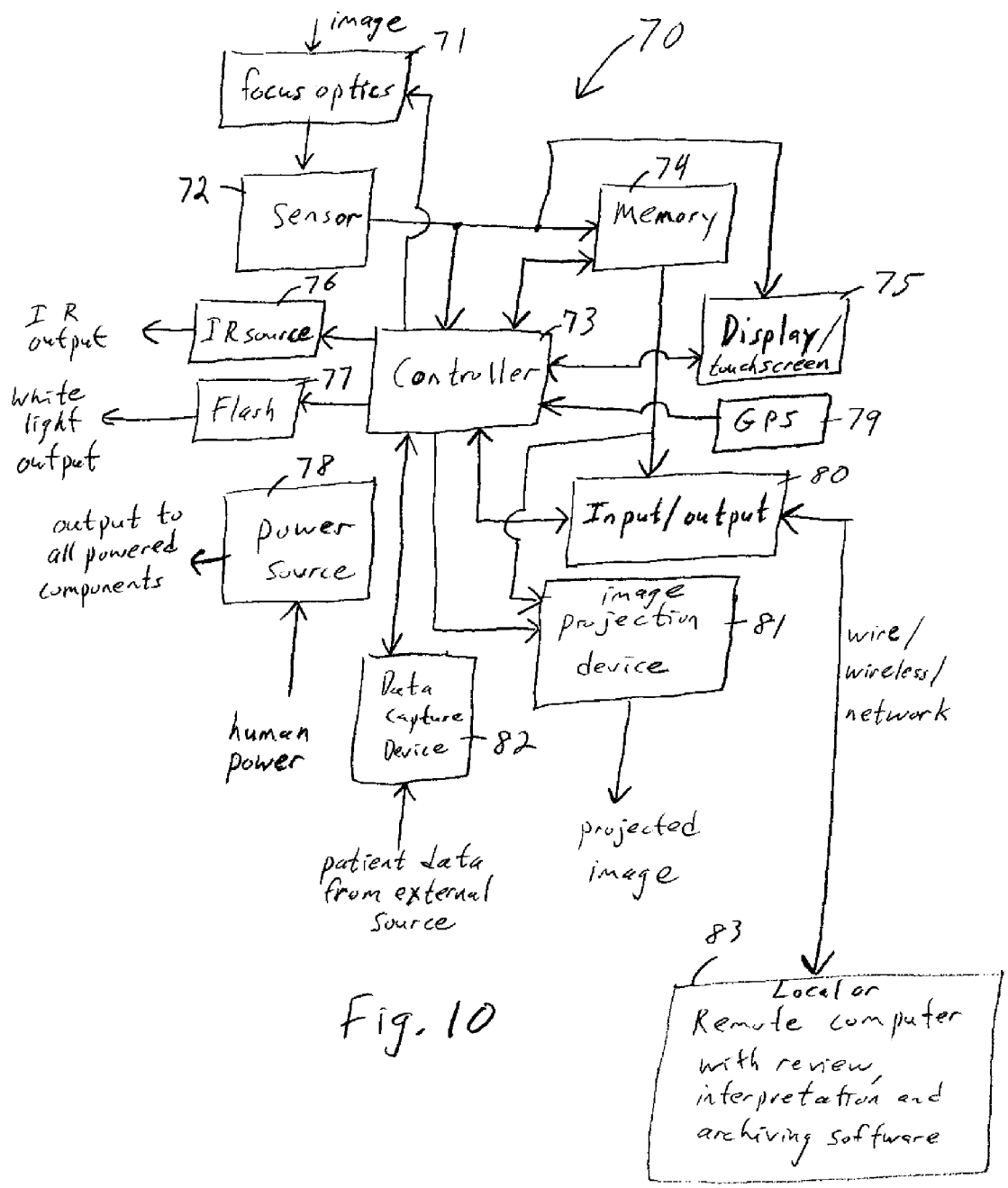
FIG. 10 is a schematic diagram of the active elements of the preferred embodiment of the invention.

FIG. 10 is a schematic block diagram of the active elements of the preferred embodiment, all of which are further described elsewhere. Camera 70 includes image focus optics 71, image sensor 72, controller 73, memory 74, display with overlaid touch screen 75, IR source 76, white light source 77, camera power source 78, GPS device 79, input/output 80, image projection device 81, data capture device 82, and local or remote computer 83.

The operating sequence for the camera is preferably as follows:

Camera power is turned on by touching power button. This function may be automated by using a touch sensor that detects when the camera has been gripped and then turns the system on. An auto-off function may also be included. For example, the system may automatically power down or go into sleep mode after a certain time has passed without input from the touch sensor or other system activity.

System opens in patient data entry mode. Required fields must be filled in before image capture sequence can be initiated. Details of data entry are discussed below. Alternatively, a bar code reader may be incorporated into the device so that patient data may be optically read from barcodes on an ID card or patient record. Another alternative is to incorporate an RFID receiver into the device so that patient information may be automatically captured when the patient is wearing an RFID tag.

Upon completion of data entry, IR illumination automatically turns on and is indicated on screen (may be turned off automatically after 60 seconds if no other commands are received)

Camera is brought up to patient's eye. While viewing screen, user aligns the camera pupil with the eye pupil. Illumination intensity is manually adjusted as the alignment is made to achieve an image with the correct brightness on the screen. Alternatively, illumination intensity may be optimized using an auto exposure circuit. In such a circuit, the illumination level on the sensor is analyzed for the mean pixel value, peak pixel values, or some combination of measurements. Exposure is then adjusted by changing amplifier gain, sensor integration time, the power to the illumination source, or a combination of these. This can occur very rapidly.

When alignment and brightness are set, user looks at PIP and adjusts focus. Alternatively, an auto focus feature may be incorporated. For example, the image may be analyzed for spatial frequencies while a motorized focusing lens is moved in and out. That lens position where high spatial frequencies are maximized is the point of best focus. This focusing can occur very rapidly.

When focus, field, and brightness are properly set, user squeezes image-capture button. IR illumination is automatically turned off and the white flash then triggers automatically, with its energy determined by the IR setting at time button is pressed. As an alternative to a manual capture button, the system may be configured for auto capture whenever certain imaging requirements are satisfied. Requirements may include correct exposure, correct focus, and correct alignment. Several images may be automatically captured in rapid sequence to improve the likelihood that at least one good image is captured.

Captured images are automatically displayed on the screen for a short period (perhaps 10 seconds) for review. The PIP is automatically off during image review.

When review period is over, system provides a series of prompts about taking another picture. If no more pictures are taken, system automatically goes into a power saving mode after a set time period (perhaps 1 minute).

Cycle is repeated by initiating step 1 again.

The control electronics accomplish the following functionality:

Control the charge coupled device (CCD) sensor

Control the flash energy

Accept control signals from the user control buttons and output appropriate commands to the image sensor, the IR illuminator, the flash circuit, and the display Communicate with an alpha-numeric touch screen for data input Perform required processing of the image, possibly including red subtraction Format the image for display, including a picture-in-picture (PIP) mode and variable magnification Compress the image per the JPEG2000 or other image compression standard Format and store the picture per the DICOM or other communication standard Send the images to the system's modem, cellular link, Internet interface, or other communication port, and control the transmission of the images to a remote location.

This controller is a printed circuit board assembly within the main camera housing. It contains a microprocessor and a variety of specialty integrated circuits. Non-volatile memory holds the operating firmware for the system.

The default display mode during image alignment, focusing, and capture has the PIP in the upper right corner of the display. The PIP has a magnification 3-4 times the whole field magnification. When reviewing images that have already been captured, the PIP is automatically turned off. The whole field image is displaced to the left by mounting the image sensor slightly off-axis horizontally.

If an advanced user wants to change the screen settings, a routine may be called up that electronically divides the screens into multiple zones. The user may use a finger or stylus to select any of these zones using the touch screen that overlays the display. The user may select a different location for the region of interest that is used for focusing, the location where the PIP window is displayed, and the magnification in the PIP. It is also possible to display patient data in the corner below the PIP.

Touch screens are used over many kinds of displays, ranging from Palm Pilots to restaurant cash registers. They provide an easy way for a user to enter data into an electronic system without the need for a mouse or mechanical keypad. A number of touch screen technologies are commercially available. In the preferred embodiment, the "4 wire resistive" technology was chosen for several reasons:

Accepts use of both a conductive stylus or a finger for selection

Very low current draw during activation, making it a better choice for hand held/battery operated designs Fewer physical layers, optimizing image clarity and overall brightness Low cost The minimum LCD display size to allow accurate data entry is a 3" diagonal. The touch panel of the display may optionally be coated with an anti-reflection coating to minimize any reflections from room lighting. The touch screen is used for a variety of functions, including:

Patient data entry

Optional camera control settings

Image review and transmission

Troubleshooting

Help menu

When the camera is first turned on, the screen automatically goes into patient data entry mode. All patient data is entered with a stylus and the "virtual keyboard", very similar to the Palm Pilot interface. After each field is entered, the user only has to touch the enter "button" and the data entry is automatically indexed to the next field. When all fields are entered, the device prompts the user to confirm that the data is correct. Alternatively, a bar code reading function may be incorporated into the device to automatically capture patient data from a hospital or insurance card, patient record, or other barcode label. This will minimize data entry errors. Another alternative is to incorporate an RFID receiver that will capture patient data automatically from an RFID tag.

During the retinal exam, the touch screen may also be used to select right or left eye and to make other settings. Alternatively, the swiveling illumination housing may incorporate a sensor to determine it's orientation, this orientation determines whether a left or right eye is being imaged.

After image capture, the screen is used for image file organization and file transfer to remote locations. The file organization screen includes a "SELECT" button, file "DELETE" button, "AND" button to allow multiple files to be processed at the same time, alpha-numeric buttons, and "SEND" button to send file(s) to a remote location.

Alternatively, an image projector may be incorporated into the device. This projector forms an enlarged image on an external surface such as a screen or wall. It may have a resolution comparable to that of the image sensor so that all of the detail in the full image is viewable at once. This is useful for confirming the quality of captured images. It is also useful as an educational tool for patients, and for accompanying medical students and practitioners. In the preferred embodiment, such a projector comprises a broadband light source, micro display, and projection lens. The light source may comprise white or multicolored LEDs or a lamp. The micro display may comprise a liquid crystal display (LCD), a digital light projector (DLP), or similar device. These devices form images from stored data files. The projection lens forms a magnified image of the micro display on a surface at a distance.

Image stabilization technology may be incorporated for removing the effects of unwanted movement during imaging. These technologies are offered in commercially available camcorders and binoculars. They eliminate the need for touching the patient in any way with the camera.

One stabilization method is a purely electronic compensation means. The image at the CCD is cropped so that the displayed field of view is smaller than the active area. Then as the camera moves, image analysis software calculates where the field of view needs to be shifted in order to offset the movement. This method requires a sensor with a larger resolution than the desired image resolution.

A second stabilization method is an optical compensation means. This uses two parallel plates separated by a bellows filled with a fluid with a high index of refraction. Vibration sensors detect movement and magnetic actuators separate the plates. Separating the plates forms a wedge, which bends the optical axis. The bending of the axis is controlled to counteract the movement of the device. This approach doesn't compromise the usable number of pixels on the sensor. However, it has the potential to impart chromatic aberrations to the image. Since the vibration sensors are located in the device, the stabilizer only compensate for the user's hand movement, and not movement of the patient.

An example of the electronic compensation technology is found in the Panasonic PV-DV951 digital camcorder, while the optical compensation means is found in the CANON 15X50IS binoculars. The stabilizer may be implemented so that it only activates when the image capture control is depressed halfway. This activates the image stabilization only when it's needed, simplifying operation, reducing processor burden, and limiting power consumption.

Images of the retina are sometimes taken with an optical filter inserted into the optical path to eliminate red wavelengths from the image. The red-free filter is used to examine the blood vessels in fine detail. By filtering out the red rays, blood vessels are silhouetted black against a dark green background. This aids in diagnoses of diabetic and hypertensive retinopathy, and well as micro aneurisms. This red subtraction can be done through digital image processing.

Many color image sensors use an array of tiny rectangular filters in a mosaic (checkerboard) configuration where each filter transmits either red, blue, or green to the pixel below. If the signal from all the red pixels is electronically removed, the resulting image is similar to using a red absorbing optical filter.

In normal sensor operation, pixel data is converted to an ROB (Red Green Blue) signal, and each pixel has R, G, and B components. The pixel color information is processed to determine the color at each pixel location based on the color at adjacent pixels. Ideally the best method to create a red free image is to set the "Red" pixel values to zero before this process is performed. This could occur just after the pixels are converted from the mosaic to RGB. When this color information is in this RGB state, the red color component may be stripped from each pixel by passing it through a digital signal processor.

This process may also be used to subtract green or blue, if this has clinical value.

Hardware and software are used to access and modify stored images. Functions may include indelible patient identification within each image file, and image compression for rapid transmission to a local or remote location. An advanced image compression algorithm such as JPEG-2000 may be used. Compression also allows for a greater number of images to be stored in the internal memory. Existing picture archiving and control system (PACS) software can interface the output of the camera to a computer network at a remote location. Appropriate controls to ensure security and error checking for data integrity may be included. A control command allows the user to specify which files to send.

What is claimed is:

1. A hand-held digital camera for obtaining images of a portion of a patient's body, comprising:
   a hand-held housing designed to be placed close to the portion of a patient's body being imaged;
   a visible light source located within the housing for providing light along an illumination path from a housing aperture to the patient's body;
   an image sensor located within the housing that detects light returning from the patient's body along an imaging path that passes into the housing aperture;
   an optical system located within the housing with separate illumination and imaging paths;
   an external optical aperture common to the illumination and imaging systems, wherein illumination and imaging sub-apertures are wholly contained within the common external aperture, are longitudinally coincident, and are laterally separated and non-overlapping;
   a digital memory device for storing captured images;
   an output display carried by the housing; and
   a means of electronically transmitting stored images.

2. The camera of claim 1, further comprising an infrared light source located within the housing that is used during alignment and focusing of the image.

3. The camera of claim 2, further comprising means for automatically adjusting the infrared irradiance.

4. The camera of claim 3, further comprising means for automatically setting the visible illuminance based on the infrared irradiance.

5. The camera of claim 1 further comprising an internal power source that enables cordless operation.

6. The camera of claim 1 further comprising means of operating on wind-up or other human-input energy that enables cordless operation.

7. The camera of claim 1 in which the field of view of the camera is at least about 30 degrees.

8. The camera of claim 7 in which the large field of view is accomplished by using an objective lens with large entrance aperture and high numerical aperture.

9. The camera of claim 7 in which the illumination field exceeds the field of view.

10. The camera of claim 1 in which the illumination and imaging fields are combined using a beamsplitter in close proximity to the housing aperture.

11. The camera of claim 1 in which the camera is used to image the fundus of the eye, and the illumination path and the imaging path both pass through the pupil plane and are separated in the pupil plane.

12. The camera of claim 11 in which the housing portion containing at least some of the illumination optics wraps around the subject's cheek in the temporal direction, so that relatively large optics can be placed in proximity with the eye without interfering with the nose or cheek.

13. The camera of claim 11 in which, in order for the camera to be used for both left and right eyes, the housing defines an illumination assembly that is adapted to swivel around the optical axis of the imaging objective lens.

14. The camera of claim 11 in which the images of the illumination and imaging apertures do not overlap at the pupil plane.

15. The camera of claim 14 in which at the pupil plane the illumination aperture is about 1 mm in diameter and the imaging aperture is about 2 mm in diameter.

16. The camera of claim 1 that accomplishes at least a plus or minus 10 diopter range of focus adjustment.

17. The camera of claim 1, further comprising a template on the display to assist the user in aligning the camera with the portion of the patient's body being imaged.

18. The camera of claim 1, further comprising means for communicating directly with a nearby computer.

19. The camera of claim 1, further comprising a user-operated image focus.

20. The camera of claim 1, further comprising a touch screen over the display.

21. The camera of claim 1, further comprising means to electronically filter one or more wavelengths from the image.

22. The camera of claim 1, further comprising means to electronically stabilize the image.

23. The camera of claim 1 in which a picture-in-picture simultaneously displays the whole field and a segment of the field at higher magnification.

24. The camera of claim 23, further comprising means for the user to select a segment of the field for displaying in a picture-in-picture.

25. The camera of claim 1, further comprising a large area image sensor to limit optical magnification and thereby reduce device size.

26. The camera of claim 1, further comprising means for automatically adjusting the visible illuminance.

27. The camera of claim 1, further comprising means for projecting stored images.

28. The camera of claim 20, further comprising templates on the touch screen to aid in entering commands or data.

29. The camera of claim 1, further comprising a barcode reader for automatically capturing data from a barcode.

30. The camera of claim 1, further comprising an RFID receiver for automatically capturing data from an RFID transmitting device.

31. The camera of claim 1, further comprising an infrared receiver for automatically capturing data from an infrared transmitting device.

32. The camera of claim 1, further comprising means for automatically focusing the image.

33. The camera of claim 1, further comprising means for automatically capturing the image when one or more predetermined conditions are satisfied.

34. The camera of claim 33, further comprising means for automatically capturing multiple images in rapid sequence.

35. The camera of claim 1, further comprising means for automatically capturing multiple images in rapid sequence.

36. The camera of claim 35, further comprising electronic means for automatically selecting captured images that satisfy one or more predefined conditions.

37. The camera of claim 1, further comprising an easily transportable headrest for the patient.

38. The camera of claim 37, further comprising replaceable parts or covers for parts of the camera or bead rest that contact the patient.

39. The camera of claim 1, further comprising a mechanism for mechanically stabilizing the camera relative to the patient.

40. The camera of claim 1, further comprising means for protecting the privacy of patient data with at least one of password protecting images and encrypting images.

41. The camera of claim 1, further comprising one or more polarizers in the illumination path and one or more polarizers in the imaging path to decrease specular reflections from the patient.

42. The camera of claim 1, in which the visible light source comprises a broadband light source, and further comprising means for filtering the light from the source, to illuminate the patient with different spectral bands.

43. The camera of claim 1, further comprising a global positioning sensor.

44. The camera of claim 1, further comprising means for indelibly embedding evidentiary data into images.

45. The camera of claim 1, in which the camera is used to image the external auditory canal.

46. A method that allows a remotely-located expert to interpret an image of a portion of a patient's body, comprising:
   a) providing a hand-held camera comprising:
      a hand-held housing designed to be placed close to the portion of a patient's body being imaged;
      a visible light source located within the housing for providing light along an illumination path from a housing aperture to the patient's body;
      an image sensor located within the housing that detects light returning from the patient's body along an imaging path into the housing aperture;
      an optical system located within the housing with separate illumination and imaging paths;
      an external optical aperture common to the illumination and imaging systems, wherein illumination and imaging sub-apertures are wholly contained within the common external aperture, are longitudinally coincident, and are laterally separated and non-overlapping;
      a digital memory device for storing captured images;
      an output display carried by the housing;
      a means of electronically transmitting stored images;
   b) using the camera to capture an image of the portion of a patient's body being imaged;
   c) providing a computer with a display device at a remote location; and
   d) transmitting the captured image over a network to the remote computer, for interpretation by an expert.

47. The method of claim 46, further comprising application software in the computer that facilitates the review, interpretation, and archiving of images.

* * * * *

UNITED STATES PATENT AND TRADEMARK OFFICE
CERTIFICATE OF CORRECTION

PATENT NO.        : 7,448,753 B1  
APPLICATION NO.   : 11/458610  
DATED             : November 11, 2008  
INVENTOR(S)       : Randal B. Chinnock Page 1 of 1

It is certified that error appears in the above-identified patent and that said Letters Patent is hereby corrected as shown below:

Claim 38, Col. 20 line 4 should be corrected as follows:

parts or covers for parts of the camera or "bead" --head-- rest that contact

Signed and Sealed this

Sixth Day of January, 2009

JON W. DUDAS  
*Director of the United States Patent and Trademark Office*